US012788413B2

(12) United States Patent
Fierlbeck et al.

(10) Patent No.: US 12,788,413 B2
(45) Date of Patent: Nov. 10, 2026

(54) MEDICAL KIT COMPRISING A DRILL AND A DEBRIS COLLECTOR

(71) Applicant: PMU INNOVATIONS GMBH, Salzburg (AT)

(72) Inventors: Johann Fierlbeck, Salzburg (AT); Michael Krieghofer, Salzburg (AT)

(73) Assignee: PMU INNOVATIONS GMBH, Salzburg (AT)

( * ) Notice: Subject to any disclaimer, the term of this patent is extended or adjusted under 35 U.S.C. 154(b) by 0 days.

(21) Appl. No.: 18/817,987

(22) Filed: Aug. 28, 2024

(65) Prior Publication Data

US 2024/0415556 A1 Dec. 19, 2024

Related U.S. Application Data

(63) Continuation of application No. PCT/EP2023/051056, filed on Jan. 18, 2023.

(30) Foreign Application Priority Data

Mar. 1, 2022 (EP) .................................... 22159430

(51) Int. Cl.
*A61B 17/16* (2006.01)

(52) U.S. Cl.
CPC ...... *A61B 17/1633* (2013.01); *A61B 17/1615* (2013.01); *A61B 2017/1651* (2013.01); *A61B 2217/007* (2013.01)

(58) Field of Classification Search
CPC ............ B23Q 11/0071; B23B 11/0042; A61B 17/1633; A61B 17/1651
See application file for complete search history.

(56) References Cited

U.S. PATENT DOCUMENTS 2,278,886 A * 4/1942 Langbein ............... B23Q 11/10 29/DIG. 75
2,478,846 A * 8/1949 Smith ................ B23Q 11/1007 408/59

(Continued)

FOREIGN PATENT DOCUMENTS

CN 108127797 A 6/2018
DE 2050573 A1 6/1972

(Continued)

OTHER PUBLICATIONS

Safety Data Sheet, Aquagel® Lubricating Gel, Parker Laboratories, Inc., US Department of Labor Occupational Safety and Health Administration, 4 Pages. 2024.

(Continued)

*Primary Examiner* — David W Bates
(74) *Attorney, Agent, or Firm* — Seager, Tufte & Wickhem LLP

(57) ABSTRACT

The present invention relates to a medical kit for use with a drilling device, the kit comprising a drill and a medical debris collector, the debris collector comprising a container, wherein the container comprises a first compartment at least partially filled with a collecting agent, the first compartment and collecting agent being configured for at least partially enclosing the drill to thereby collect drilling debris in the container and the collecting agent during a drilling process.

17 Claims, 14 Drawing Sheets

(56) References Cited

U.S. PATENT DOCUMENTS

| | | | | |
|---|---|---|---|---|
| 2,548,314 | A * | 4/1951 | Kinney, Sr. | B23Q 11/0064 29/DIG. 95 |
| 2,847,880 | A * | 8/1958 | Neidig | B23Q 11/10 62/DIG. 10 |
| 3,339,435 | A | 9/1967 | Heitz | |
| 3,890,860 | A * | 6/1975 | Gordon | B23B 13/08 82/163 |
| D285,618 | S | 9/1986 | Borgman | |
| 4,891,037 | A * | 1/1990 | Maples | F16G 13/02 184/15.1 |
| 5,061,123 | A | 10/1991 | Broussard | |
| 5,087,158 | A * | 2/1992 | Devine | B23Q 11/0053 408/241 B |
| 5,160,230 | A | 11/1992 | Cuevas | |
| 5,201,615 | A * | 4/1993 | Patterson | B23B 35/005 408/87 |
| 5,653,561 | A | 8/1997 | May | |
| 5,765,654 | A | 6/1998 | Burger | |
| D437,667 | S | 2/2001 | Hwang | |
| D509,333 | S | 9/2005 | Tash | |
| D542,312 | S | 5/2007 | Skradski et al. | |
| D542,313 | S | 5/2007 | Skradski et al. | |
| D543,563 | S | 5/2007 | Skradski et al. | |
| D588,893 | S | 3/2009 | Radich | |
| D590,227 | S | 4/2009 | Yun | |
| 7,549,826 | B2 * | 6/2009 | Videtto | B23Q 11/0042 408/202 |
| 8,016,522 | B2 * | 9/2011 | Chen | B23B 49/026 408/56 |
| 9,073,161 | B2 | 7/2015 | Tseng | |
| D774,865 | S | 12/2016 | Chen | |
| 2005/0047880 | A1 * | 3/2005 | Seely | B23Q 11/0053 408/67 |
| 2010/0298835 | A1 | 11/2010 | Ralph et al. | |
| 2013/0094915 | A1 | 4/2013 | Chen | |
| 2014/0037392 | A1 | 2/2014 | Lo | |
| 2016/0375535 | A1 * | 12/2016 | Joern | B23B 35/00 408/1 R |
| 2017/0000500 | A1 | 1/2017 | Thomas | |
| 2018/0021859 | A1 * | 1/2018 | Rivat | B23Q 11/0071 408/1 BD |
| 2025/0090177 | A1 * | 3/2025 | Dillard | A61B 17/1633 |
| 2025/0127525 | A1 * | 4/2025 | Wilson | A61B 17/1642 |

FOREIGN PATENT DOCUMENTS

| | | | |
|---|---|---|---|
| DE | 2229446 | A1 | 1/1974 |
| DE | 19738400 | A1 | 3/1999 |
| DE | 1020050587981 | B3 | 11/2006 |
| EP | 1714735 | A1 | 10/2006 |
| KR | 200406694 | Y1 | 1/2006 |
| WO | 9716118 | A1 | 5/1997 |
| WO | 2010012767 | A1 | 2/2010 |

OTHER PUBLICATIONS

Clinical® Ultraschall-Gel Product Sheet, 1 Page. 2024. aaa.

Extended European Search Report for EP Application 221594302, dated Aug. 8, 2022. (8 Pages).

Operace Product Data Sheet, Mastering Implant Removal, DePuy Synthes, Companies of Johnson&Johnson, 28 Pages. Dec. 15, 2015.

International Search Report and Written Opinion for International Application No. PCT/EP2023/051056, dated Mar. 21, 2023. (10 Pages).

* cited by examiner

MEDICAL KIT COMPRISING A DRILL AND A DEBRIS COLLECTOR

PRIORITY DATA

This application is a continuation of International Application No. PCT/EP2023/051056, filed Jan. 18, 2023, which claims priority to EP Application No. 22159430.2, filed Mar. 2, 2022, the contents of which are herein incorporated by reference in their entirety.

TECHNICAL FIELD

The present invention relates to a medical kit comprising a drill and a debris collector. The present invention also relates to a method of assembling a drill and a debris collector according to the invention with a drilling device and to a method of performing a surgical screw head removal procedure.

BACKGROUND

Implant removal is a common surgical procedure. Implants are often fixed to the bones of patients with implant screws. Accordingly, during an implant removal procedure, a surgeon needs to loosen and remove the implant screws in order to be able to remove the implant. However, during this procedure, the surgeon has to deal with damaged screw heads and cold welded screw-plate interfaces. In some cases, it is not possible to use standard implant removal screw drivers to remove such screws. Instead, the surgeon needs to drill out the screw head and/or the whole screw using a drilling device and a drill.

During the drilling process, drilling debris is created. As the screws and implants are usually made from metal and/or metal alloys, it is necessary to avoid the situation that drilling debris enters the patient's body—or at least ensure a reduction of the amount of drilling debris entering the body as far as possible. Current techniques focus on rinsing the working zone, e.g., with physiological NaCl solution and aspirating the drilling debris together with the salt solution. However, these techniques have several drawbacks. As the surgeon is occupied with drilling out the screw, a second person is required to do the rinsing and aspiration of the debris, which makes the procedure more complicated. The drilling process itself is more of a punctual nature, but the rinsing and aspiration tend to distribute the particles in a 3-dimensional way. Moreover, depending on the skills of the person doing the rinsing and aspiration, a certain amount of drilling debris may still enter the patient's body and can cause health risks.

BRIEF SUMMARY

It is an object of the present invention to provide improved tool accessories for improving implant removal procedures. This and other objects are achieved with the claimed invention as recited in the claims.

BRIEF DESCRIPTION OF THE DRAWINGS

The invention will be further described with reference to the figures. The figures show embodiments of the invention and are not to be understood in a limiting way.

DETAILED DESCRIPTION

Figure 1A:
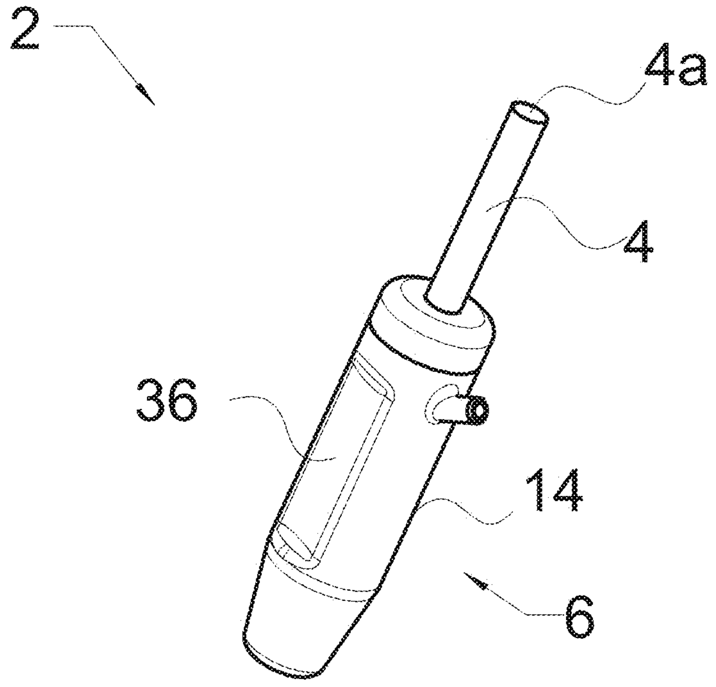
FIG. 1A shows a schematic overview of a kit comprising a drill and debris collector according to the invention.

It is an object of the present invention to provide improved tool accessories for improving implant removal procedures. This and other objects are achieved with the claimed invention as recited in the claims.

The present invention relates to a medical kit for use with a drilling device, the kit comprising a drill and a medical debris collector, the debris collector comprising a container, wherein the container comprises a first compartment at least partially filled with a collecting agent, the first compartment and collecting agent being configured for at least partially enclosing the drill to thereby collect drilling debris in the container and the collecting agent during a drilling process.

The drilling device may be a drilling machine and cordless or with cord. The drill may be a drill for surgical screw removal and/or a carbide drill and/or a high-speed steel (HSS) drill. Despite the fact that the term "drill" is also used in the art as a short expression for "drilling machine", the term "drill" as used herein refers to the, generally exchangeable, tool piece that is configured for being grasped by the chuck of a drilling machine and for contacting the workpiece. The drill may be a single piece. Alternatively, the drill may be composed of two or more pieces as known in the art, e.g., a holder configured for insertion into the chuck and a bit for insertion into the holder. The holder and bit may be configured for quick release and insertion as known in the art. Preferably, the drill is configured to convey drilling debris in a helical path generally along its longitudinal axis and away from the workpiece during drilling. For example, the drill may comprise one, preferably two or more flutes as known in the art.

During a drilling process drilling debris is created by the drill removing chips from the workpiece, e.g., an implant screw. The drill may transport the drilling debris along the drill's longitudinal axis. The drilling debris is then collected in the debris collector, particularly in the collecting agent. The collecting agent may be a gel.

Depending on the material and the duration of the procedure, heat production resulting from drilling may require cooling of the working zone, i.e., the workpiece, e.g., a screw to be drilled out, and the drill. The container may comprise a second compartment, wherein the second compartment is configured for providing a cooling agent for the drilling process. Optionally, the second compartment is an elongate lumen. The cooling agent may be sterile water or a solution comprising sodium, e.g. physiological NaCl solution, Ringer's solution or a variant of sodium solution, e.g. sodium lactate solution, or balanced salt solution. The material of the cooling agent may be the same as the material of the collecting agent. Independently of whether there is provided a second compartment and a cooling agent or not, the collecting agent may also contribute to transporting heat away from the drilling zone.

The container may comprise a first wall defining the first compartment. Optionally, the container comprises a second wall defining the second compartment. The first wall and/or the second wall may have any suitable shape. One or more portions of the first wall may at the same time be (a) portion(s) of the second wall and/or vice versa. In other words, the first compartment and the second compartment may have common wall portions. For example, a wall portion separating the first and second compartments from each other may be such a common wall portion.

The container may be a single piece or comprise two or more pieces.

The container and the collecting agent may be configured for enclosing at least a portion of a working section of the drill. The container may comprise one or more contact zones, which are configured to contact the drill. Other portions of the container may be configured to not contact the drill. For example, the first compartment may be defined by a wall, the wall being configured to not contact the drill except for the contact zones. Working section refers to the portion of the drill that is configured for removing material from a workpiece. For example, in the case of a drill comprising flutes, the portion of the drill comprising the flutes may be its working section. In addition to the working section, a drill may also comprise a non-working section which is not configured for processing a workpiece. The non-working section of the drill may comprise a shank, which may be configured to be grasped in the chuck of a drilling device. The end of the drill that is configured for being inserted into the drilling device is also referred to as the proximal end. The other end of the drill is referred to as the distal end of the drill. Generally, proximal/proximally refers to something that is closer to an operator of the drill, debris collector and drilling device during a drilling process than something that is distal/distally located.

The kit may be configured such that the drill traverses the collecting agent during a drilling process. Preferably, the drill is at least partially in contact with the collecting agent during a drilling process. The container and the collecting agent may be configured such that the portion of the working section that is enclosed by the collecting agent is in contact with the collecting agent. Preferably, the kit is configured such that a portion of the drill distal of and adjacent the chuck is free of collecting agent. This may ensure that the drilling device is not contaminated with and/or damaged by collecting agent entering the chuck and may be reused. The kit may be configured such that during a drilling process the distal end of the drill extends distally from the collecting agent or is flush with the collecting agent—this depends on the specific configuration of the drill and its working section as well as the specific configuration of the debris collector and the workpiece.

The container may comprise a distal opening that is located at a distal portion of the first compartment, wherein the container is configured to house at least the portion of the working section of the drill within the first compartment such that a distal tip of the drill may contact a workpiece at the distal opening and/or distal of the distal opening. The distal opening is optionally closed with a removable closure before insertion of the drill into the distal opening and configured to be opened by removing the removable closure.

Alternatively, the first compartment may comprise a distal portion, wherein the distal portion is configured for being drilled through by the drill. In this case, an operator may, after optionally introducing the drill of the kit into the debris collector, use the drill for drilling the distal opening prior to the actual drilling process, e.g. for screw removal.

The container may comprise a proximal opening that is located at a proximal portion of the first compartment. The container may be configured to house at least the portion of the working section of the drill within the first compartment such that a proximal portion of the drill extends proximally from the proximal opening. Preferably, the proximal opening is proximal of the working section.

The container may comprise at least one outlet in fluid communication with the second compartment and an exterior of the debris collector, the debris collector being configured to provide the cooling agent to a drilling zone of a workpiece during a drilling process via the outlet. Preferably, the outlet is located in a distal region of the container.

As already mentioned, the collecting agent may be a gel. The term "gel" may be used for a semi-solid system comprising a cross-linked phase and a fluid phase. The collecting agent being a gel may contribute to a reduction of collecting agent leaking out of the distal opening and/or the container. Preferably, the collecting agent is a surgical gel and/or an ultrasound gel and/or a catheter gel. For example, the following commercially available gels are suitable:

- CLINICAL® Ultraschall-Gel currently produced by Ultragel Hungary 2000 Kft., 1211-Budapest, Tekercselő u. 12. Hungary, and currently distributed by Diagramm Halbach GmbH & Co. KG, Am Winkelstück 14, 58239 Schwerte, Germany; ingredients: water, carbomer, sodium hydroxide, EDTA, methylisothiazolinone, chlormethylisothiazolinone, benzyl alcohol, colorless or E 131 or Aloe;
- MERGO® Ultrasound gel-currently produced by megro GmbH & Co. KG, Am Schornacker 30, 46485 Wesel, Germany; ingredients: Aqua dest., Cabomer, Glycerol 85%, Sodium Hydroxide, Propylene Gly-col, Benzyl Alcohol, Methylchloroisothiazolinone, Methylisothiazolinone, Citric Acid;
- AQUASONIC® 100 ULTRASOUND TRANSMISSION GEL currently produced by PARKER LABORATORIES INC., 286 ELDRIDGE ROAD, FAIRFIELD, NJ 07004 USA;
- SCAN® ULTRASOUND GEL currently produced by PARKER LABORATORIES INC., 286 ELDRIDGE ROAD, FAIRFIELD, NJ 07004 USA;
- AQUASONIC® 100 STERILE ULTRASOUND currently produced by PARKER LABORATORIES INC., 286 ELDRIDGE ROAD, FAIRFIELD, NJ 07004 USA;
- OPTILUBE® currently produced by Optimum Medical Solutions Limited, Tennant Hall Blenheim Grove Leeds West Yorkshire United Kingdom LS2 9ET;
- AQUAGEL® LUBRICATING GEL currently produced by PARKER LABORATORIES INC., 286 ELDRIDGE ROAD, FAIRFIELD, NJ 07004 USA;

The kit may be configured such that, at least before use, the first compartment is filled with collecting agent to a certain degree. A limit for the filling level may be given by the necessity of providing an initially free volume in the container that is configured to be filled with drilling debris during a drilling process and optionally cooling agent during a drilling process.

As the geometry of the container and the first compartment can vary the following relations may have to be taken into account concerning the volume of the collecting agent. The internal volume of the first compartment is preferably determined considering the following aspects:

- The basic geometry of the medical debris collector/the container and the drill, determined by the handling and the operating conditions.
- The volume of the drill itself
- The expected drilling depth
- The expected volume of chips that will be released during the drilling process, depending on the drilling depth
- The amount of collecting agent around the working section of the drill to achieve a proper sealing function.

The filling volume of the collecting agent in the first compartment may be determined according to the following considerations. The free inner volume of the first compartment must be able to accommodate the volume of the collecting agent and the volume of the drilling debris that arise during the drilling process. The drilling depth and the diameter of the drill determine the volume of the drilling debris. The shape and length of the container and the first compartment determine the available internal volume. Subtracting the volume of the drilling debris from the free inner volume of the first compartment results in the maximum volume available for the collecting agent. Starting from the tip of the drill, the drill should be surrounded along its longitudinal axis at least over a length of 2 times d with collecting agent, so that the collecting agent has the desired effect.

In an ideally designed kit, there is sufficient volume available in the first compartment for the drilling debris of the desired drilling process. The remaining volume of the first compartment is preferably filled with collecting agent. Preferably the drill is covered at least 2 times d along its longitudinal axis starting from the distalmost point of the first compartment, wherein d is the diameter of the drill, with the kit assembled and with the drill's longitudinal axis oriented vertically and with the drill tip located below the drill's proximal end (also referred to as upright orientation). The kit is preferably configured such that, in the upright orientation, the proximal end(s) of the flute(s) of the drill is/are located distally of the filling level of the collecting agent. Thus, the collecting agent remains in the distal portion of the container during a vertically progressing drilling process. Thus, the flutes are covered with collecting agent during such a drilling process, with the advantage that the collecting agent and the drilling debris remain in the distal zone and are not hurled into the initially collecting agent-free volume.

Additionally or alternatively, the kit may be configured such that, at least before use, at least ¼, preferably at least ⅓ of the volume of the first compartment is filled with the collecting agent.

Using the kit in a drilling process may alter the volume that is occupied by the collecting agent. For example, the volume may be affected by shearing processes that occur during drilling due to the drill rotating within the collecting agent. Additionally or alternatively, the volume of the collecting agent may be affected by an increasing temperature due to a drilling process.

The collecting agent may be a shear thinning or shear thickening material in the relevant regime. In a shear thickening material, which is also called dilatant material, the viscosity increases with the shear rate. In a shear thinning material, the viscosity decreases with shear rate.

The collecting agent may be a heat thinning or heat thickening material in the relevant regime. In analogy to "shear thickening", in a heat thickening material, the viscosity increases with temperature. In analogy to "shear thinning", in a heat thinning material, the viscosity decreases with temperature.

The collecting agent may be configured for use in a human and/or animal body. Preferably, the collecting agent is non-toxic to the human and/or animal body. For example, the commercially available gels mentioned above are configured for use with the human body and are non-toxic for the human body.

The collecting agent may have a viscosity of 10,000-3,000,000 mPas (cP). The commercially available gels have viscosities in this range.

The container and/or the collecting agent and/or the cooling agent may be transparent. The transparency may refer to visible light including certain wavelengths and/or wavelength ranges of visible light. The material may be considered transparent, if the transmission of the relevant wavelength(s) is sufficient for a chosen observation technique, e.g. observation by eye. Preferably, the whole container is transparent. Alternatively, the container is partially transparent. Preferably, the portions of the container that are located along a viewing axis to the working section of the drill are transparent. This is advantageous because an operator performing a drilling procedure may survey the process, e.g. the movement of the drill, the destruction process of the workpiece and the take-up of drilling debris, and may react accordingly, e.g. in case of any anomality or when the drilling process has sufficiently advanced.

The debris collector may be adapted for relative rotation between the container and the drill. This may result in the debris container and/or the container having lower rotational velocity than the drill during a drilling process. Particularly, the container may not rotate during a drilling process. For example, during a drilling process, the operator may grasp the container and hold the container in place while the drill is rotating. Inter alia for this purpose, the container may comprise a grip configured to be grasped by an operator's hand.

The container may have a longitudinal axis and the container may be, at least at portions of the longitudinal axis, rotationally symmetric about its longitudinal axis. Alternatively or additionally, the outer surface of the container may be, at least along portions of the longitudinal axis, rotationally symmetric about the longitudinal axis. For example, the outer shape of the container may be a cylinder or an ellipsoid. At certain locations, the container may have one or more indentations and/or one or more projections to an otherwise rotationally symmetric shape. For example, the grip may comprise one or more indentations and/or one or more projections. Additionally or alternatively, the second compartment may be a lumen attached to the outside of a cylinder, the cylinder comprising and or/being the first compartment. It is noted that the term "longitudinal axis of the container" refers to the axis that is configured to coincide with the longitudinal axis of the drill during a drilling process, even if the shape of the container does not have its major dimension along this axis.

The container may be intrinsically and/or extrinsically rigid. Optionally, the container is free of rubber. "Intrinsic" is used for a flexibility/rigidity that results from material properties such as atomic/molecular bonds, three-dimensional structures of molecules and the like. "Extrinsic" is used herein for flexibility/rigidity that results from a mechanical and/or geometric configuration on a scale larger than material scale, e.g. a bellow structure, hinges, and/or a telescope mechanism. “Rigid” in the present context means, that the container is free of any intrinsic or extrinsic elements to adapt to a changing availability of space during a drilling process. For example, the available space for the container decreases, when the drill sinks into the workpiece, which results in the chuck of the drilling machine approaching the workpiece. Thus, the space between the chuck and the workpiece, which is where the container is located, becomes smaller. With a rigid container, the drill hole may be limited by the length of the drill that may extend distal of the container.

The drill may comprise, as already mentioned, a non-working section, e.g. a shank, and the container may include a drill guide, wherein the drill guide is configured to be located at the non-working section. The drill guide may be configured as a bearing for the drill during a drilling process. For example, the proximal opening of the container may be configured as a drill guide. For example, an operator may grasp the debris collector with one hand and grasp and operate the drilling device with the other hand, thus stabilizing the drill during a drilling process.

The container may be configured to move along a longitudinal axis of and relative to the drill during a drilling process. This may mean that the container may move and/or be moved proximally and/or distally along the drill. For example, during a drilling process, it may be advantageous to keep the container as close to the working zone/drill tip as possible. However, with increasing progress of the drilling process, the drill tip sinks into the workpiece. Accordingly, assuming the container was installed flush or almost flush with the distal tip of the drill at the beginning of the drilling process, the container may not remain in this position but has to move posteriorly in order to not block the sinking of the drill into the workpiece.

The container may have dimensions which are adapted to the diameter of the drill configured to be housed within the container. For surgical reasons and for handling reasons an outer diameter of the container is preferably 18 mm or less and/or at least 10 mm, i.e. the outer diameter of the container is most preferably in the range of 10 mm to 18 mm. Preferably, this applies to any outer diameter of the container. The diameter is measured orthogonally with respect to the longitudinal axis of the container.

The length of the container is limited by the drill length. In general, the container and/or the whole debris collector has to be shorter than the drill in order to provide an interface area to the drilling device. For rigid containers, the length of the container and/or drilling device is also limited in that it must provide the desired working depth of the drill. The length of the container is measured as the largest spatial extent parallel to its longitudinal axis, which is configured to correspond to the longitudinal axis of the drill.

The container's distal portion may have a distally tapering shape, e.g. a cone like shape. The full circumference or one or more portions of the circumference may have the distally tapering shape. For example, the container may have the shape of a cone, wherein the second compartment breaks through the shape of the cone. Cone like shape includes also truncated cone like shape. Distally tapering may mean that, moving distally along the outer surface, the radius decreases. As explained in detail below with reference to the figures, such shape may be advantageous for angulated drilling.

The debris collector and the drill may be configured for single use and/or may be sterile.

The debris collector may comprise any suitable material. The container may comprise a material that is configured for shape adaption at a temperature T that is above room temperature and is generally reached at the distal tip of the container during a surgical drilling process. Such temperature T may be in a range of 100° C.-200° C., 110° C.-190° C., 120° C.-180° C., 140° C.-160° C., 110° C.-130° C., 150° C.-170° C., and/or 170° C.-190° C. Particularly, the temperature may be T=120° C., T=160° C., or T=180° C. Room temperature is defined as 16° C. to 23° C. A suitable material may be selected from the group of thermoplastics, e.g. polypropylene and/or polyethylene, each with properties suitable for human and/or animal surgery. An advantage of such shape adaption properties may be as follows: Upon drilling, heat is generated. The heat is either created at or partially transferred to the container, e.g. at the distal tip and/or the distal opening of the container. The heat causes the material at the container's tip to soften, i.e. to start to melt, while still maintaining sufficient stability for the drilling process. When a user pushes the container, i.e. the tip, against the workpiece, the softened tip adapts its shape to the shape of the abutting workpiece. Moreover, the softened material may provide a gluing effect. Thus, a sealing effect is provided, which may further improve the efficiency of the debris collector.

The present invention also relates to a method of assembling a drilling device with a drill and a medical debris collector as specified herein, comprising the steps:

a) providing the drilling device, the drill and the debris collector;
b) fixing the drill in the drilling device;
c) optionally slipping the debris collector with the first compartment at least partially filled with collecting agent over the drill, such that the drill traverses the debris collector from a proximal opening to a distal opening of the container and such that the first compartment and collecting agent at least partially enclose the drill.

Step c) may not be necessary in every embodiment, for example in embodiments where the drill and the debris collector are provided with the debris collector being already assembled, e.g. slipped on the drill such that the drill traverses the debris collector from a proximal opening to a distal opening of the container and such that the first compartment and collecting agent at least partially enclose the drill.

The alphabetic numbering of the steps has been chosen to name the steps differently in order to be able to refer to the different steps without reciting their complete wording. Particularly, the order of the method steps may not be as indicated by the alphabetic numbering. For example, step c) may be carried out after and/or concurrently with step b). Alternatively, step b) may be carried out after and/or concurrently with step c). Step a) may be carried out before step b) and/or step c).

The method may comprise the steps:

c1) providing the distal opening in the container of the debris collector by
  i. removing a removable closure from the preformed distal opening; or
  ii. drilling the distal opening into the container.

The present invention also relates to a method of performing a surgical screw head removal procedure comprising the steps:

A) drilling out a screw head with a drilling device with a drill and a mounted debris collector as specified herein;
B) maintaining the debris collector close to the screw;
C) collecting drilling debris in the debris collector;

D) optionally providing cooling agent to the screw head and the dill.

Again, the alphabetic numbering of the steps has been chosen to name the steps differently in order to be able to refer to the different steps without reciting their complete wording. Particularly, the order of the method steps may not be as indicated by the alphabetic numbering. Particularly, steps A), B), C) and D) may be carried out concurrently. Step D) may be carried out intermittently and as necessary.

Step C) may particularly include collecting the drilling debris in the collecting agent.

The following aspects are preferred embodiments of the invention:

1. A medical kit for use with a drilling device, the kit comprising a drill and a medical debris collector, the debris collector comprising a container, wherein the container comprises a first compartment at least partially filled with a collecting agent, the first compartment and collecting agent being configured for at least partially enclosing the drill to thereby collect drilling debris in the container and the collecting agent during a drilling process.
2. The kit of aspect 1, wherein the container comprises a second compartment, wherein the second compartment is configured for providing a cooling agent for the drilling process, optionally wherein the second compartment is an elongate lumen.
3. The kit of aspects 1-2, wherein the container and the collecting agent are configured for enclosing at least a portion of a working section of the drill.
4. The kit of any one of the preceding aspects, wherein the container is configured such that the drill traverses the collecting agent during a drilling process, preferably wherein the drill is at least partially in contact with the collecting agent during a drilling process.
5. The kit of aspects 3 or 4, wherein
    a. the container comprises a distal opening that is located at a distal portion of the first compartment, wherein the container is configured to house at least the portion of the working section of the drill within the first compartment such that a distal tip of the drill may contact a workpiece at the distal opening and/or distal of the distal opening, wherein the distal opening is optionally closed with a removable closure before insertion of the drill into the distal opening and configured to be opened by removing the removable closure; or
    b. the first compartment comprises a distal portion, wherein the distal portion is configured for being drilled through by the drill.
6. The kit of aspects 3-4, wherein the container comprises a proximal opening that is located at a proximal portion of the first compartment, wherein the container is configured to house at least the portion of the working section of the drill within the first compartment such that a proximal portion of the drill extends proximally from the proximal opening, preferably wherein the proximal opening is proximal of the working section.
7. The kit of aspects 2-6, wherein the container comprises at least one outlet in fluid communication with the second compartment and an exterior of the debris collector, the debris collector being configured to provide the cooling agent to a drilling zone of a workpiece during a drilling process via the outlet; preferably wherein the outlet is located in a distal region of the container.

8. The kit of any one of the preceding aspects, wherein the collecting agent is a gel, preferably a surgical gel and/or an ultrasound gel and/or a catheter gel.
9. The kit of any one of the preceding aspects, wherein at least ¼, preferably at least ⅓ of the volume of the first compartment is filled with the collecting agent; and/or
   in the upright orientation, a filling level of the collecting agent in the first compartment is 2 d, wherein d is the diameter of the drill.
10. The kit of any one of the preceding aspects, wherein the collecting agent is configured for use in a human and/or animal body, preferably non-toxic to the human and/or animal body.
11. The kit of any one of the preceding aspects, wherein the collecting agent has a viscosity of 10,000-3,000,000 mPas.
12. The debris collector of any one of the preceding aspects, wherein the container and/or the collecting agent and/or the cooling agent is/are transparent.
13. The kit of any one of the preceding aspects, wherein the debris collector is adapted for relative rotation between the container and the drill.
14. The kit of any one of the preceding aspects, wherein the container is intrinsically and/or extrinsically rigid, and optionally wherein the container is free of rubber.
15. The kit of any one of the preceding aspects, wherein the drill comprises a non-working section, e.g. a shank, and wherein the container includes a drill guide, wherein the drill guide is configured to be located at the non-working section.
16. The kit of any one of the preceding aspects, wherein the container is configured to move along a longitudinal axis of and relative to the drill during a drilling process.
17. The kit of any one of the preceding aspects, wherein the drill is a drill for surgical screw removal and/or a carbide drill and/or a HSS drill.
18. The kit of any one of the previous aspects, wherein the container has an outer diameter of 18 mm or less, and/or at least 10 mm.
19. The kit of any one of the preceding aspects, wherein the debris collector and the drill are configured for single use and/or are sterile.
20. The kit of any one of aspects 5-19, wherein the container's distal portion has a distally tapering shape, e.g. a cone like shape.
21. The kit of any one of the preceding aspects, wherein the container comprises a material that is configured for shape adaption at a temperature T in a range of 100° C.-200° C., 110° C.-190° C., 120° C.-180° C., 140° C.-160° C., 110° C.-130° C., 150° C.-170° C., and/or 170° C.-190° C., particularly at T=120° C., T=160° C., or T=180° C., e.g. a thermoplastic, e.g. polypropylene and/or polyethylene.
22. A method of assembling a drilling device with a drill and a medical debris collector, preferably as specified in the kit of any one of the aspects 1 to 21, comprising the steps:
    d) providing the drilling device, the drill and the debris collector;
    e) fixing the drill in the drilling device;
    f) optionally slipping the debris collector with the first compartment at least partially filled with collecting agent over the drill, such that the drill traverses the debris collector from a proximal opening to a distal opening of the container and such that the first compartment and collecting agent at least partially enclose the drill.

23. The method of the previous aspect, comprising the steps:
   c1) providing the distal opening in the container of the debris collector by
      i. removing a removable closure from the preformed distal opening; or
      ii. drilling the distal opening into the container.

24. A method of performing a surgical screw head removal procedure comprising the steps:
   E) drilling out a screw head with a drilling device with a drill and a mounted debris collector as specified in the kit of any one of aspects 1 to 21;
   F) maintaining the debris collector close to the screw;
   G) collecting drilling debris in the debris collector
   H) optionally providing cooling agent to the screw head and the drill.

Figure 1B:
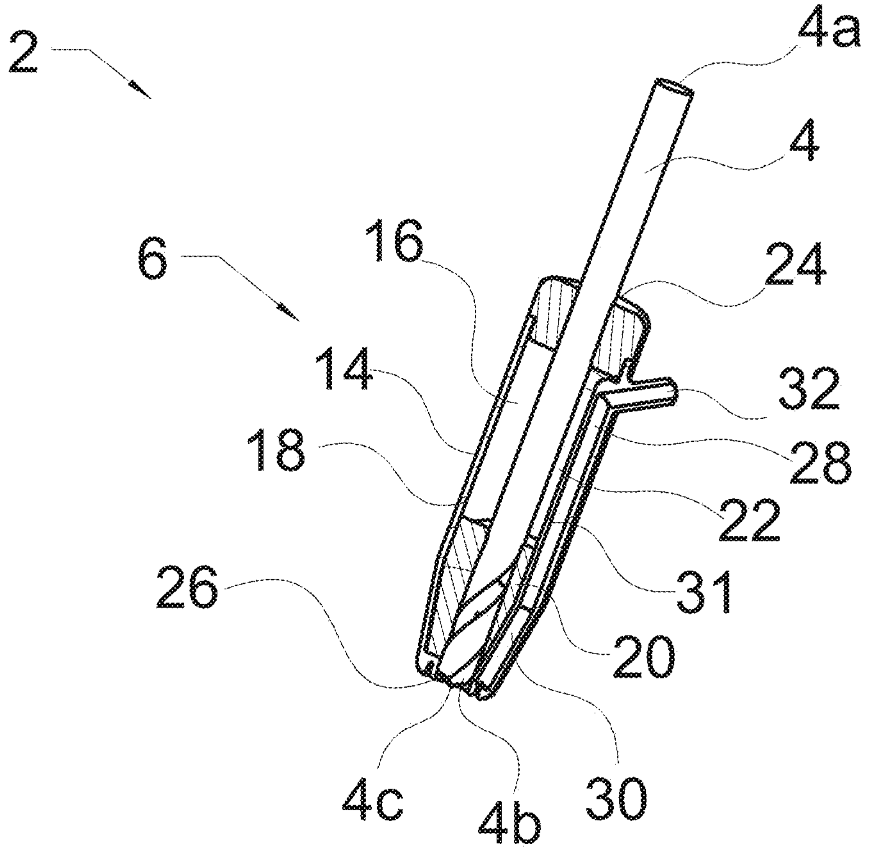
FIG. 1B shows a cross section of the kit of FIG. 1A.
Figure 1C:
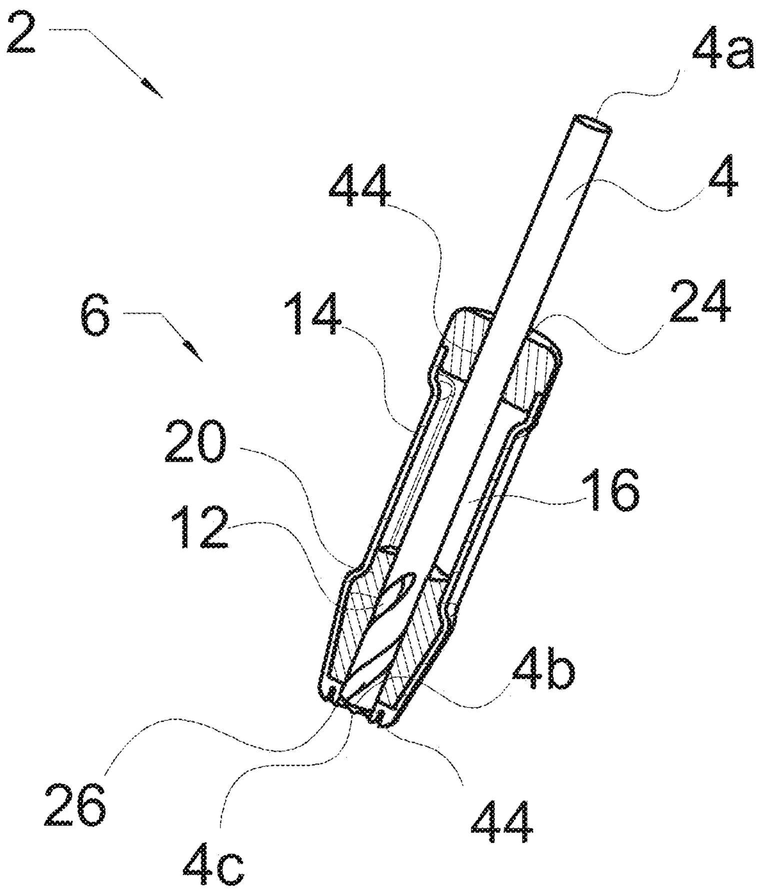
FIG. 1C shows another cross section of the kit of FIG. 1A at an angle of 90° with the cross section of FIG. 1B.
Figure 3:
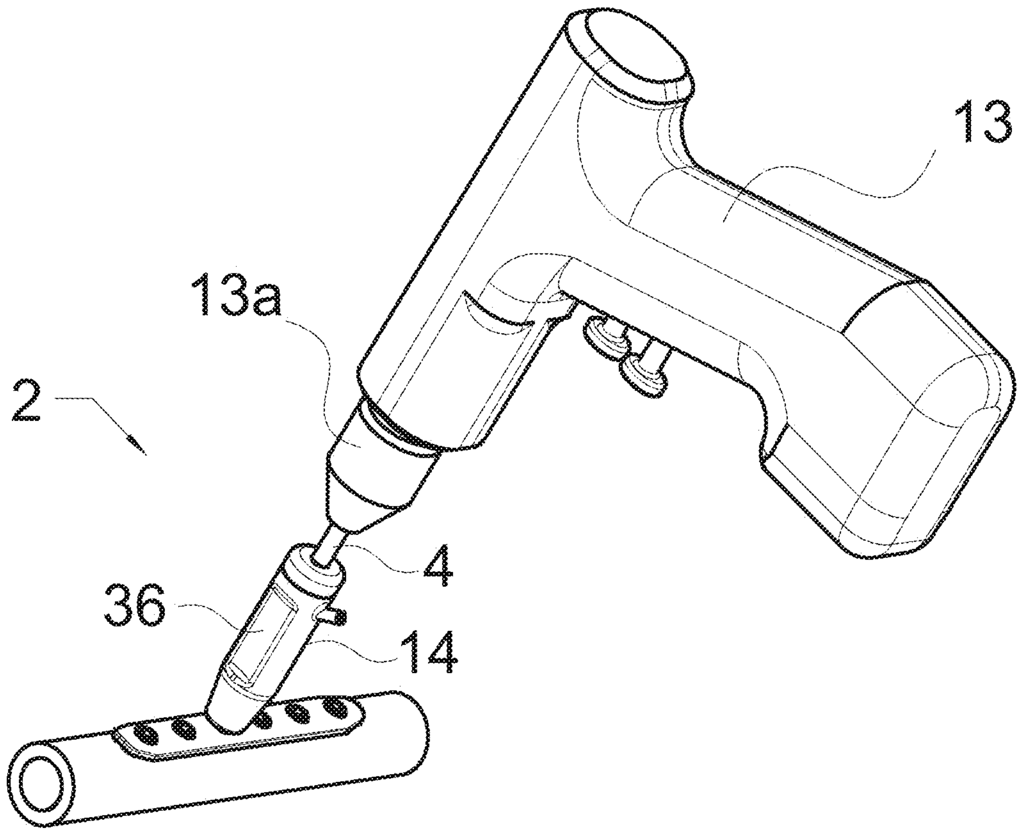
FIG. 3 shows a debris collector assembled with a drill according to the present invention and coupled to a drilling device.
Figure 4A:
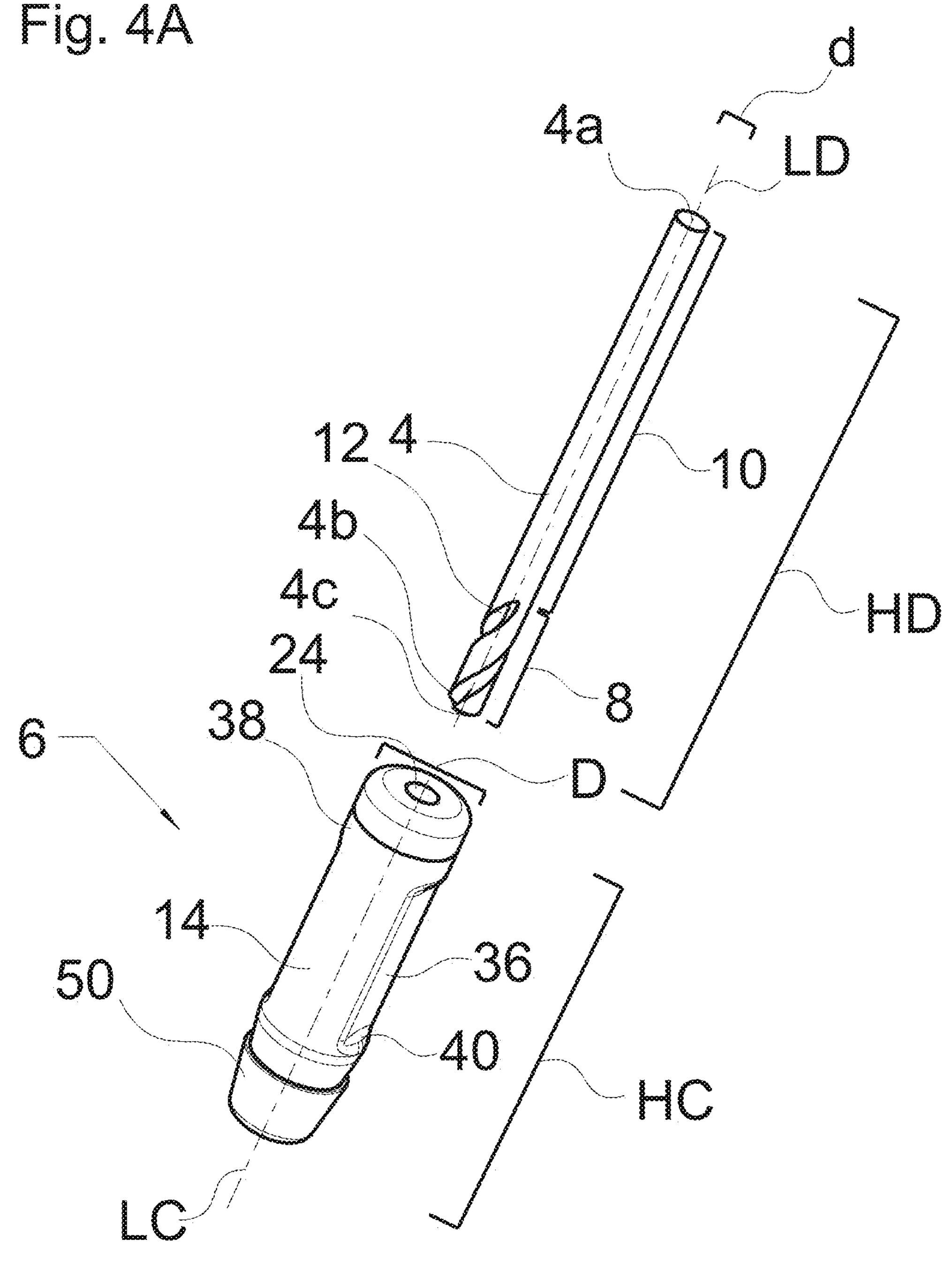
FIG. 4A shows a debris collector and a drill in a disassembled state.

Turning to the Figures, FIG. 1A shows a schematic overview of a kit 2 comprising a drill 4 and debris collector 6 according to the invention. FIGS. 1B and 1C show cross sections of the kit 2 along a longitudinal axis of the drill 4, which include an angle of 90°. FIG. 4A shows the drill 4 and the debris collector 6 separated from one another. The drill 4 may be a drill 4 for surgical screw removal and/or a carbide drill 4 and/or a HSS drill 4. The drill 4 has a proximal end 4*a* and a distal end 4*b* including a distal tip 4*c*. The drill 4 has a working section 8 and a non-working section 10. As shown, the working section 8 may be defined as the portion of the drill 4 that comprises flutes 12, while the non-working section 10 may be defined as the portion of the drill 4 that is free of flutes 12. As shown in FIG. 3, the proximal end 4*a* and at least a part of the non-working section 10, i.e. a shank, are configured for insertion into a chuck 13*a* of a drilling device 13.

During a drilling process (see FIGS. 2A-2C), i.e. processing a workpiece 7, drilling debris 9 is created by the drill 4 removing chips from the workpiece 7, e.g. an implant screw 7. The drill 4 conveys the drilling debris 9 proximally and the drilling debris 9 is then collected in the debris collector 6.

The size of the debris collector 6 may be adapted to the size of the drill 4. The debris collector 6 comprises a container 14. The container 14 may have a size that fits the drill 4. A length HC of the container (as defined above) may be equal to or smaller than the length HD of the drill 4, as measured along its longitudinal axis LD. Preferably, an outer diameter D of the container 14 is 10 mm-18 mm, preferably any outer diameter D of the container 14 is 10 mm-18 mm.

As shown in the Figures, the container 14 comprises a first compartment 16 defined by a first wall 18. The first compartment 16 comprises collecting agent 20, which is shown to partially fill the first compartment 16. For example, the volume occupied by the collecting agent 20 may correspond to a filling level in the first compartment 16 of 2*d as measured in the upright orientation of the kit, i.e. from the distalmost point of the inner surface of the first compartment 16. d is the diameter of the drill 4. Preferably, the collecting agent has a volume corresponding to one third of the volume of the first compartment 16. Other filling levels are possible. A limit for the filling level may be given by the necessity of providing an initially free volume 22 in the first compartment 16 that is configured to be filled with drilling debris 9 and optionally cooling agent (further explained below with reference to FIG. 2*c*) during a drilling process.

As already mentioned, the collecting agent 20 may be a gel and particularly one of the gels mentioned herein. The collecting agent 20 may be configured for use in a human and/or animal body. Preferably, the collecting agent 20 is non-toxic to the human and/or animal body. The collecting agent may have a viscosity of 10,000-3,000,000 mPas (cP). The container 14 and/or the collecting agent 20 and/or the cooling agent 30 may be transparent in the wavelength regime visible to the human eye as explained herein.

The container 14 may comprise a proximal opening 24 and a distal opening 26. As shown in the figures, the proximal opening 24 of the container 14 may also be a proximal opening of the first compartment 16 and the distal opening 26 of the container 14 may also be a distal opening of the first compartment 16. The proximal opening 24 and the distal opening 26 may be configured to receive the drill 4. In an assembled state, and when the drill 4 and the debris collector 6 are ready for drilling, the drill 4 and the debris collector 6 may be arranged as shown in FIGS. 1B, 1C, 2B and 2C, i.e. with the drill 4 traversing the container 14, the first compartment 16 and the collecting agent 20. Thus, the first compartment 16 and the collecting agent 20 are configured for at least partially enclosing the drill 4 to thereby collect drilling debris 9 in the container 14. In an assembled state, the distal opening 26 may be located slightly proximal of the distal tip 4*c* of the drill 4. The portion 8*a* of the working section 8 that extends distally beyond the distal opening 26 of the container 14 is effectively doing the drilling in the workpiece 7. For further reference it is called effective working section 8*a*. The portion of the drill 4 that extends proximally from the proximal opening 24 of the container 14 includes the shank for insertion into a chuck 13*a* of a drilling device 13 (see FIG. 3). Preferably, the proximal opening 24 is configured to be located proximal of the working section 8 of the drill 4 when assembled.

As shown in FIG. 1B, the container 14 may comprise a second compartment 28, wherein the second compartment 28 is configured for providing a cooling agent 30 for the drilling process. The second compartment 28 may be defined by a second wall 31. As shown, the first and second walls 18, 31 may have common portions. Optionally, the second compartment 28 is an elongate lumen as shown in the Figures. The cooling agent 30 may be sterile water or a solution comprising sodium, e.g. physiological NaCl solution, Ringer's solution, sodium lactate solution, or balanced salt solution.

The second compartment 28 may comprise an inlet 32 configured for providing cooling agent 30 from a reservoir (not shown) to the second compartment 28. The container 14 may comprise at least one outlet 34 in fluid communication with the second compartment 28 and an exterior of the debris collector 6, the debris collector 6 being configured to provide the cooling agent 30 to a drilling zone e.g. to the effective working section 8*a* of the drill 4 and the workpiece 7.

Preferably, the outlet 34 is located in a distal region of the container 14. The outlet 34 is typically located distal to the inlet 32, however, they may be at the same position along the drill 4 when installed, or the inlet 32 may be distal to the outlet 34 when installed.

The process of transporting cooling agent 30 out of the second compartment 28 via the outlet 34 to the working zone and/or filling cooling agent 30 into the second compartment 28 via the inlet 32 may be motorized, e.g. by means of one or more pumps or the like. Alternatively or additionally, the process(es) may be performed manually, e.g. by means of an assistant operating one or more syringes or the like. Particularly, adding cooling agent 30 to the second compartment 28 via the inlet 32 may cause a corresponding amount of cooling agent 30 to exit the second compartment 28 via the outlet 34. Thus, effective cooling of the drilling process may be achieved.

The debris collector 6 may be adapted for relative rotation between the container 14 and the drill 4. As shown in the figures, the debris collector 6 may be mounted to the drill 4 via the proximal opening 24 and the distal opening 26. The material of the debris collector 6 defining these openings 24, 26 may thus serve as contact zones for contacting the drill 4, and particularly as bearings. A fitting between the openings 24, 26 and the drill is preferred in order to prevent a leakage of the collecting agent 20 from the container 14. The fitting still allows for a light rotation of the debris collector 6/the container 14 relative to the drill 4. For example, during a drilling process, the operator may grasp the container 14 and hold the container 14 in place while the drill 4 is rotating. Inter alia for this purpose, the container 14 may comprise the grip 36 configured to be grasped by an operator's hand.

Figure 5A:
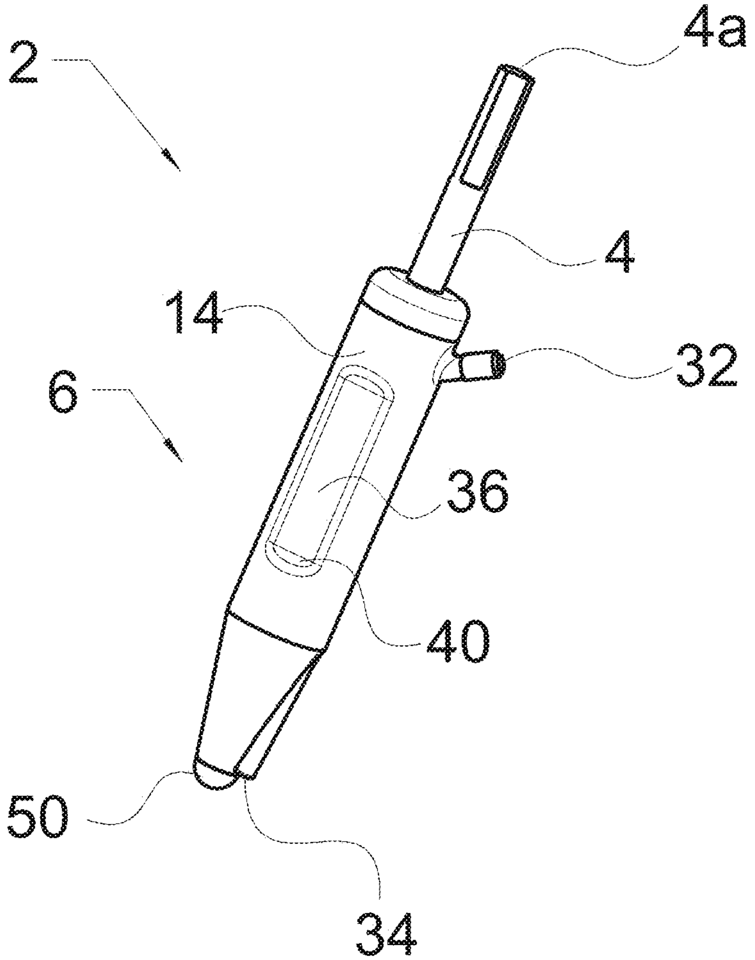
FIG. 5A shows an embodiment of a debris collector with a distal geometry adapted for drilling out angulated screws.
Figure 5B:
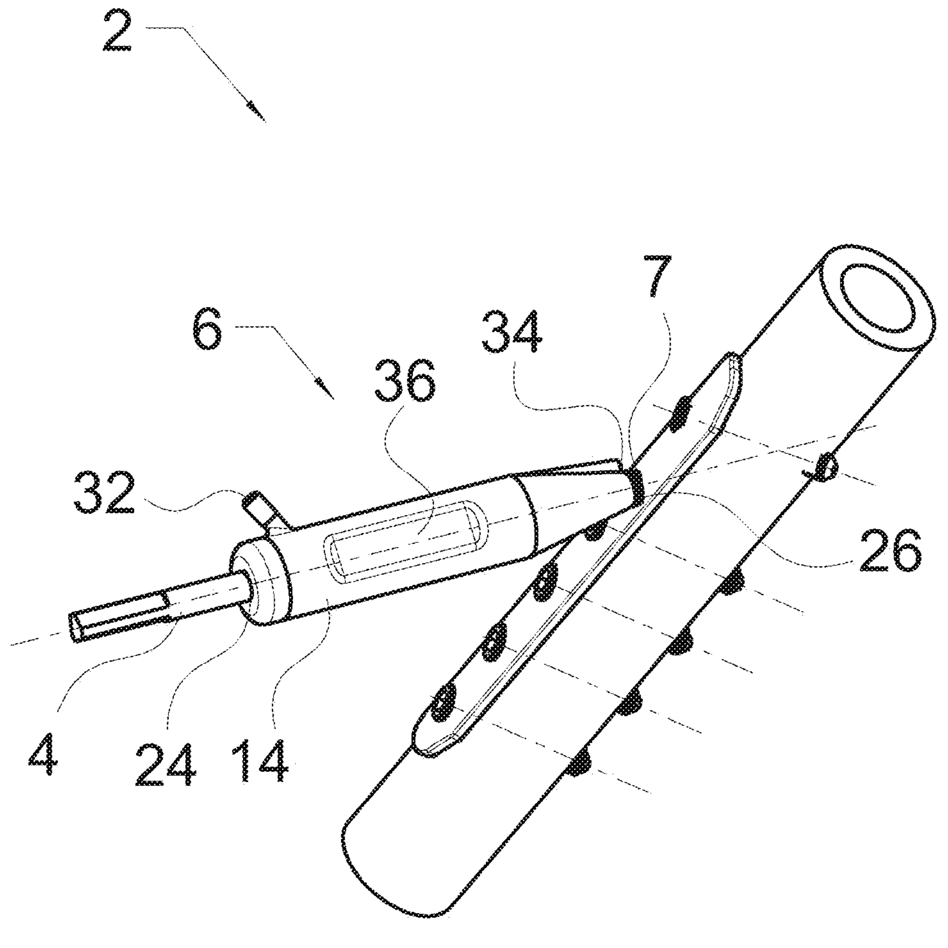
FIG. 5B shows the embodiment of FIG. 5A in use, drilling a screw fixed in a plate.
Figure 5C:
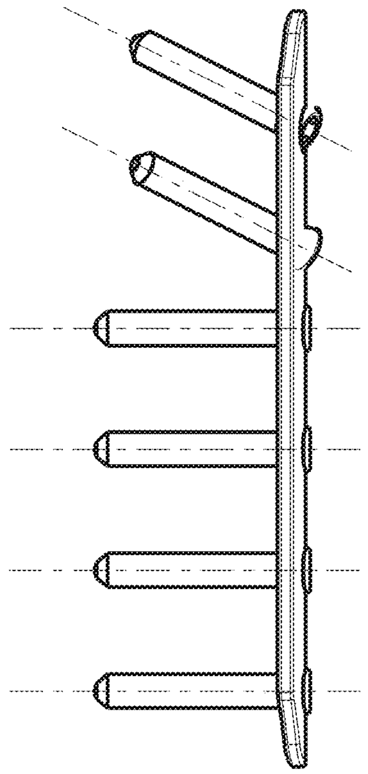
FIGS. 5C, 5D, 5E show three views, with angles of approx. 90° to each other, of the plate and screws shown in FIG. 5B.
Figure 5D:
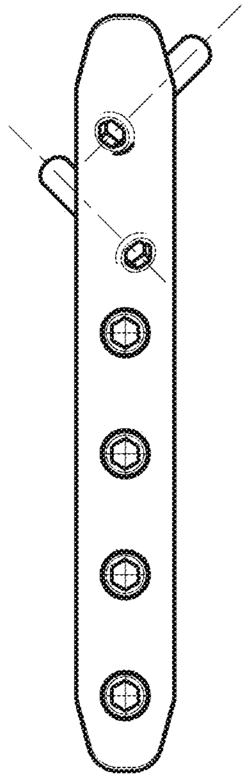
Figure 5E:
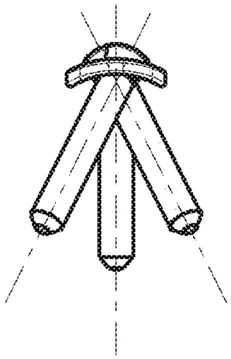

As shown in FIG. 4A, the container 14 may have a longitudinal axis LC and an outer surface 38 of the container 14 may be, at least at portions of the longitudinal axis LC, rotationally symmetric about its longitudinal axis LC. Additionally, the container 14 may be, at least along portions of the longitudinal axis LC, rotationally symmetric about its longitudinal axis LC. At certain locations, the container 14 may have one or more indentations 40 and/or one or more projections (not shown) to an otherwise rotationally symmetric surface 38. For example, the grip 36 may comprise one or more indentations 40 and/or one or more projections (not shown). Additionally or alternatively, the second compartment 28 may be a lumen attached to the outside of a cylinder, the cylinder comprising and or/being the first compartment 16. The container 14, preferably the debris collector 6, may have any suitable general shape. As shown in the figures, the container 14 may have a cylindrical shape with a distally tapering distal portion. Tapering may, e.g., occur along a straight line, as shown, and/or along a curved line. As shown in the FIGS. 5A-5E a distally tapering distal portion may be advantageous when drilling out angulated screws. Angulated screws fixing plates to bones are common in surgical practice. Such a situation is illustrated in FIGS. 5B-5E, with FIGS. 5C-5E showing three views of the plate and screws of FIG. 5B at angles of 90° to each other. As can easily be seen, some of the screws are oriented at an angle to each other, and, importantly, non-perpendicular to the convex surface of the plate. FIG. 5A shows an embodiment of a debris collector 6 with a distal geometry particularly adapted for drilling out angulated screws. The debris collector 6 and drill 4 are assembled with a chuck 13*a* of a drilling device 13. FIG. 5B shows the kit 2 of FIG. 5A in the process of drilling out one of the angulated screws. As shown, the drill 4 is preferably oriented such that it essentially follows the longitudinal axis of the screw. In other words, the longitudinal axis of the drill LD essentially coincides with the longitudinal axis of the screw to be drilled out. Accordingly, the container's longitudinal axis LC preferably coincides with the longitudinal axis of the screw to be drilled out. For this purpose, a distally tapering distal portion of the container 6 may be advantageous. In other words, the distal portion of the container 6 may have a cone-like shape. This may facilitate angulated drilling as compared to a container 6 with a completely cylindrical shape of the distal portion. As shown, the tapering is only present at a portion of the circumference of the distal portion. As shown, this may be due to the elongate second compartment, which may terminate in the second compartment's outlet 34, breaking the generally cone-like shape of the distal portion. The distal tip or termination of the container 6 may have any suitable configuration. Particularly, in its distal portion, the container may taper towards and reach a diameter, measured perpendicular to the longitudinal axis LC, that is equal to or smaller than the sum of the diameter of the distal opening 26 and the "perpendicular thickness" of the wall defining the distal opening 26, wherein the "perpendicular thickness" is measured perpendicular to the longitudinal axis LC of the container. In a view from distal to proximal and along the longitudinal axis LC of the container 6, the container's 6 wall defining the distal opening 26 may have a ring-like shape.

The container 14 may be a single piece or, as shown in the figures, be composed of two or more pieces. For example, the container 14 may be composed of two or more pieces in order to facilitate production of the debris collector and/or filling of collecting agent 20 into the first compartment 16. In the Figures the container is shown to comprise a first piece, called "main portion" and a second piece called "cap". The main portion has a cylindrical shape that has a distal, tapering portion and it constitutes a major portion of the container. The cap is shown to complete the proximal part of the container and comprising the proximal opening 24. However, this is only one example of how the container 14 may be split into two or more pieces. The distal portion may be a separate piece as well, to adapt the container to angulated or straight drilling. For example, for angulated drilling, i.e. essentially not perpendicular to a surface of a plate, the distal portion may be distally tapering. For straight drilling, i.e. essentially perpendicular to the surface of the plate, the distal portion may be non-tapering or distally tapering. Other configurations are contemplated.

The debris collector 6 may comprise, as already mentioned, a drill guide 44 that is configured to be located at the non-working section 10 of the drill 4. The drill guide 44 may be configured as a bearing for the drill 4 during a drilling process. For example, the proximal opening 24 may be configured as the drill guide 44. For example, an operator may grasp the debris collector 6 with one hand and grasp and operate the drilling device 13 (see FIG. 3) with the other hand, thus stabilizing the drill 4 during a drilling process.

Figure 2A:
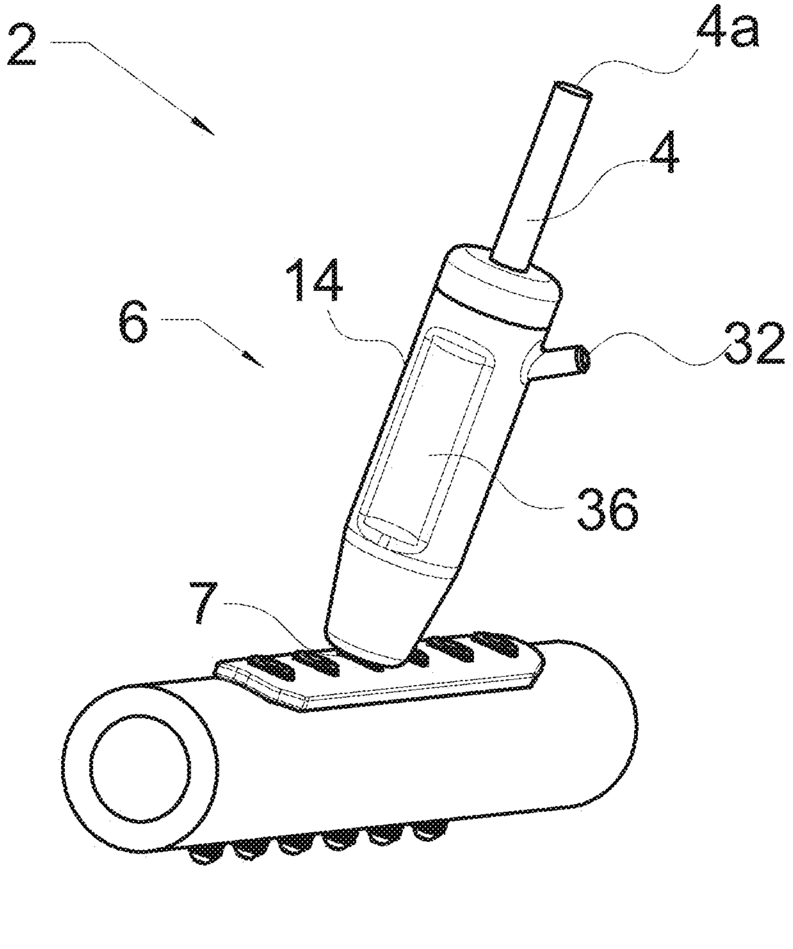
FIG. 2A shows an embodiment of a debris collector according to the invention in use.
Figure 2B:
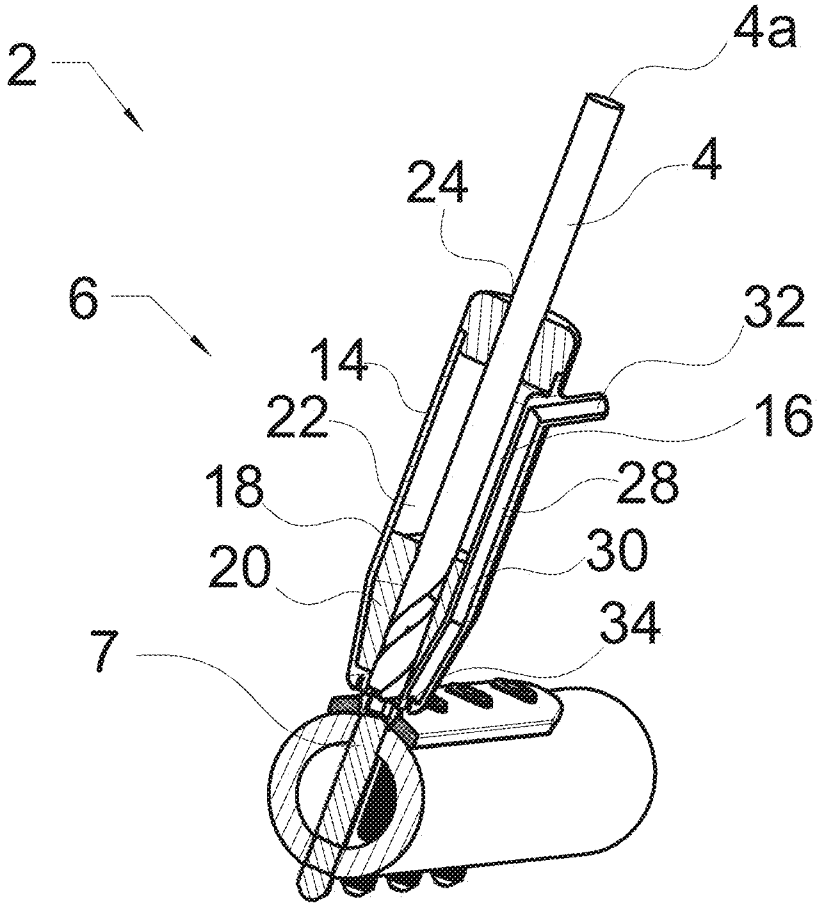
FIG. 2B shows a cross section of FIG. 2A.
Figure 2C:
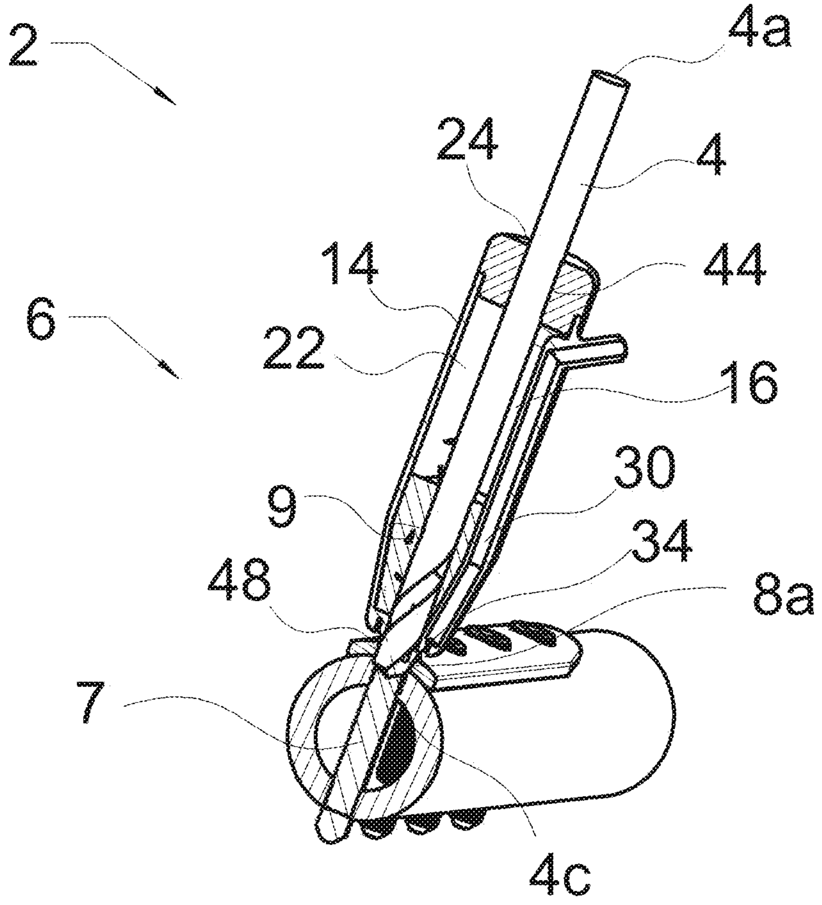
FIG. 2C shows a cross section of the ensemble of FIG. 2A drilling out a screw.

The container 14 may be configured to move along a longitudinal axis LD of the drill 4 and thus relative to the drill 4 during a drilling process. For example, the container 14 may move and/or be moved proximally and/or distally along the drill 4. For example, during a drilling process, it may be advantageous to keep the container 14 as close to the workpiece 7/drill tip 4*c* as possible. However, with increasing progress of the drilling process, the drill tip 4*c* sinks into the workpiece 7. This is illustrated in FIGS. 2A, 2B and 2C. FIG. 2A and 2B show the initial state of a drilling process in a 3D drawing and a corresponding cross sectional view, respectively, wherein the drill 4 and debris collector 6 have been assembled, the drill 4 has been put into contact with the workpiece 7 and the drilling process is about to start. In this state, the effective working section 8*a* is kept rather small, i.e. the debris collector 6 is located close to the distal tip 4*c* of the drill 4. In FIG. 2C, the drilling process has advanced to a state in which the drill tip 4*c* has created a drilling hole 48 and advanced a significant distance into the workpiece 7. Accordingly, the debris collector 6 has moved proximally along the longitudinal axis LD of the drill 4, thus allowing for the drill 4 to further penetrate the workpiece 7 and providing a larger effective working section 8*a* as compared to the state in FIG. 2*b*. Thus, the debris collector 6 may always be kept as close to the distal tip 4*c* as possible in order to collect as much drilling debris 9 as possible.

The container 14 may be intrinsically and/or extrinsically rigid. Optionally, the container 14 is free of rubber. Particularly, the container 14 may be rigid enough to essentially maintain its shape during a drilling process.

Additionally or alternatively, as already explained above, the container may comprise a material that is configured for shape adaption at a temperature in a range of 100° C.-200° C., 110° C.-190° C., 120° C.-180° C., 140° C.-160° C., 110° C.-130° C., 150° C.-170° C., and/or 170° C.-190° C. Particularly, such temperature may be T=120° C., T=160° C., or T=180° C. For example, the container material may be a thermoplastic, e.g. polypropylene and/or polyethylene.

Figure 4B:
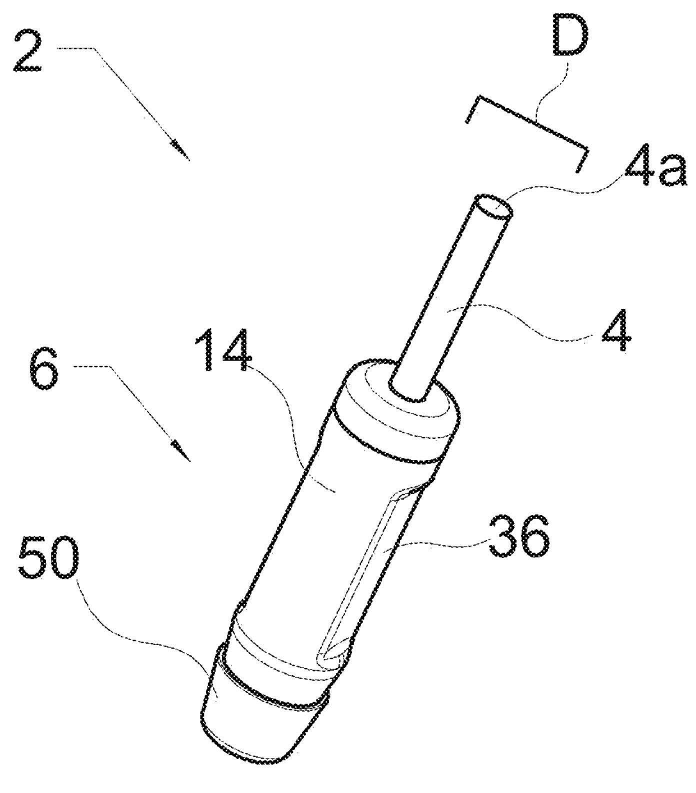
FIG. 4B shows a debris collector and a drill in an assembled state.

The debris collector 6 and the drill 4 may be configured for single use and/or may be sterile. The sterile kit 2 may be delivered to an operator in sterile packaging. Particularly, the debris collector 6 and the drill 4 may be delivered to an operator in a disassembled state (FIG. 4A), or in an assembled state (FIG. 4B). The assembly state at delivery may depend on the embodiment of the debris collector 6 and particularly on the configuration regarding the distal opening 26 and the proximal opening 24. For example, in the case of an assembled kit 2 (FIG. 4B), the debris collector 6 comprises the proximal opening 24 when being delivered to an operator, the debris collector 6 is at least partially mounted to the drill 4 and the kit 2 is ready to be mounted to a drilling device. In the case of an assembled kit 2, the debris collector 6 may house the distal end 4*b* of the drill 4 but the debris collector 6 may not yet comprise the distal opening 26 (not shown) or the distal opening 26 may be closed, e.g. by a removable closure 50 (FIG. 4B), and configured to be opened by removing the removable closure 50. If the debris collector 6 does not yet comprise the distal opening 26, the first compartment 16 may comprise a distal portion, wherein the distal portion is configured for being drilled through by the drill 4. In this case, an operator may introduce the drill 4 of the kit 2 into a drilling device 13 and use the drill 4 and the drilling device 13 for drilling the distal opening 26 prior to the actual drilling process, e.g. for screw removal. The debris collector 6 with the reversibly closed distal opening 26 or the distal portion configured for drilling through may also be delivered to an operator in a disassembled state, i.e. the operator also has to introduce the drill 4 into the debris collector 6. With disassembled delivery, the options for the proximal opening 24 are the same as for the distal opening: it may already exist upon delivery, optionally closed with a removable closure (not shown), or it may not yet exist and have to be drilled into the debris collector 6 by the operator.

Accordingly, an operator may perform the following method steps in order to assemble the debris collector 6, the drill 4 and a drilling device 13:

- a) providing the drilling device 13, the drill 4 and the debris collector 6;
- b) fixing the drill 4 in the drilling device 13;
- c) optionally slipping the debris collector 6 with the first compartment 16 at least partially filled with collecting agent 20 over the drill 4, such that the drill 4 traverses the debris collector 6 from the proximal opening 24 to the distal opening 26 of the container 14 and such that the first compartment 16 and collecting agent 20 at least partially enclose the drill 4.

Step c) may not be necessary in every embodiment, for example in embodiments where the drill 4 and the debris collector 6 are provided with the debris collector 6 being already assembled with the drill 4, e.g. slipped on the drill 4 such that the drill 4 traverses the debris collector 6 from the proximal opening 24 to the distal opening 26 and such that the first compartment 16 and collecting agent 20 at least partially enclose the drill 4.

Optionally, and depending on whether the debris collector 6 has a preformed distal opening 26, the operator may perform the following step c1) in the method:

- c1) providing the distal opening 26 in the container 14 of the debris collector 6 by
  - i. removing a removable closure 50 from the preformed distal opening 26; or
  - ii. drilling the distal opening 26 into the container 14.

In order to perform a surgical screw head removal procedure an operator may perform the following method comprising the steps:

- A) drilling out a screw head with a drilling device 13 with a drill 4 and a mounted debris collector 6 as specified herein;
- B) maintaining the debris collector 6 close to the screw 7;
- C) collecting drilling debris 9 in the debris collector 6, preferably in the collecting agent 20;
- D) optionally providing cooling agent 30 to the screw head and the dill.

The order of the steps a), b), c) and c1) as well as A), B), C) and D) has already been discussed above.

LIST OF REFERENCE SIGNS

- 2 kit;
- 4 drill;
- 4*a* proximal end of drill;
- 4*b* distal end of drill;
- 4*c* distal tip of drill;
- 6 debris collector;
- 7 workpiece;
- 8 working section of drill;
- 8*a* effective working section of drill;
- 9 drilling debris;
- 10 non-working section of drill;
- 12 flute;
- 13 drilling device;
- 13*a* chuck of drilling device;
- 14 container;
- 16 first compartment;
- 18 wall of first compartment;
- 20 collecting agent;
- 22 initially free volume of first compartment;
- 24 proximal opening of container;
- 26 distal opening of container;
- 28 second compartment;
- 30 cooling agent;
- 31 second wall;
- 32 inlet;
- 34 outlet;
- 36 grip;
- LC longitudinal axis of container;
- LD longitudinal axis of drill;
- 38 outer surface;
- 40 indentation;
- 44 drill guide:
- 48 drilling hole;
- 50 removable closure
- HC length of container;
- HD length of drill
- D outer diameter of container;
- d diameter of the drill.

What is claimed is:

1. A medical kit for use with a drilling device, the kit comprising a drill and a medical debris collector, the drill comprising a drill bit and the medical debris collector comprising a container, wherein the container comprises a first compartment at least partially filled with a first agent, the first compartment and the first agent being configured for at least partially enclosing the drill bit to thereby collect drilling debris from a workpiece in the container and the first agent during a drilling process, wherein the container comprises a second compartment, wherein the second compartment comprises an inlet configured for receiving a second agent from a reservoir and the container comprises at least one outlet in fluid communication with the second compartment and an exterior of the medical debris collector, the at least one outlet is configured for providing the second agent to a drilling zone of the workpiece distal of the first compartment to cool the workpiece during the drilling process.

2. The kit of claim 1, wherein the second compartment is an elongate lumen.

3. The kit of claim 1, wherein:

the container and the first agent are configured for enclosing at least a portion of a working section of the drill bit; and/or the container is configured such that the drill bit traverses the first agent during the drilling process, wherein the drill bit is at least partially in contact with the first agent during the drilling process.

4. The kit of claim 3, wherein:

a. the container comprises a distal opening that is located at a distal portion of the first compartment, wherein the container is configured to house at least the portion of the working section of the drill bit within the first compartment such that a distal tip of the drill bit may contact a workpiece at the distal opening and/or distal of the distal opening, wherein the distal opening is optionally closed with a removable closure before insertion of the drill bit into the distal opening and configured to be opened by removing the removable closure; or b. the first compartment comprises a distal portion, wherein the distal portion is configured for being drilled through by the drill bit.

5. The kit of claim 3, wherein the container comprises a proximal opening that is located at a proximal portion of the first compartment, wherein the container is configured to house at least the portion of the working section of the drill bit within the first compartment such that a proximal portion of the drill bit extends proximally from the proximal opening, wherein the proximal opening is proximal of the working section.

6. The kit of claim 1, wherein the first agent is one or more of a surgical gel, an ultrasound gel or a catheter gel; and/or wherein the first agent is configured for use in a human and/or animal body and is non-toxic to the human and/or animal body.

7. The kit of claim 1, wherein:

at least ¼ a volume of the first compartment is filled with the first agent; and/or in an upright orientation, a filling level of the first agent in the first compartment is 2d, wherein dis a diameter of the drill bit.

8. The kit of claim 1, wherein the medical debris collector is adapted for relative rotation between the container and the drill bit; and/or wherein the container is configured to move along a longitudinal axis of and relative to the drill bit during a drilling process.

9. The kit of claim 1, wherein the container is intrinsically and/or extrinsically rigid, and optionally wherein the container is free of rubber.

10. The kit of claim 1, wherein the drill bit comprises a non-working section and wherein the container includes a drill guide, wherein the drill guide is configured to be located at the non-working section.

11. The kit of claim 1, wherein the drill bit is a drill for surgical screw removal and/or a carbide drill and/or a high-speed steel drill.

12. The kit of claim 1, wherein the container has an outer diameter of 18 mm or less, and/or at least 10 mm.

13. The kit of claim 4, wherein the distal portion of the first compartment has a distally tapering shape.

14. The kit of claim 1, wherein the container comprises a material that is configured for shape adaption at a temperature T in a range of 100° C.-200° C., 110° C.-190° C., 120° C.-180° C., 140° C.-160° C., 110° C.-130° C., 150° C.-170° C., and/or 170° C.-190° C. particularly at T=120° C., T=160° C., or T=180° C.

15. The kit of claim 1, wherein the container is configured such that during a drilling process, adding the second agent to the second compartment via the inlet causes a corresponding amount of the second agent to exit the second compartment via the at least one outlet.

16. The kit of claim 1, wherein the container is configured such that the second agent is received at the inlet, passes through the second compartment, and exits the at least one outlet without passing through the first compartment.

17. The kit of claim 1, wherein the second compartment is laterally offset from the first compartment and extends longitudinally along the first compartment.

* * * * *